United States Patent [19]

Grasser

[11] Patent Number: 4,838,248

[45] Date of Patent: Jun. 13, 1989

[54] SHOCK WAVE HEAD FOR NON-CONTACTING DISINTEGRATION OF CALCULI

[75] Inventor: Franz Grasser, Eggolsheim, Fed. Rep. of Germany

[73] Assignee: Siemens Aktiengesellschaft, Berlin and Munich, Fed. Rep. of Germany

[21] Appl. No.: 133,283

[22] Filed: Dec. 11, 1987

[30] Foreign Application Priority Data

Dec. 22, 1986 [DE] Fed. Rep. of Germany ....... 3643971

[51] Int. Cl.⁴ ............................................. A61B 17/22
[52] U.S. Cl. ................................... 128/24 A; 128/328
[58] Field of Search ......................... 367/150; 73/642; 128/24 A, 328, 660

[56] References Cited

U.S. PATENT DOCUMENTS 3,800,276  3/1974  Rishell .
4,194,510  3/1980  Proudian .
4,340,944  7/1982  Dory ............................... 367/150 X
4,476,873  10/1984 Sorenson et al. .................... 128/660
4,674,505  6/1987  Pauli et al. .

*Primary Examiner*—Ruth S. Smith
*Attorney, Agent, or Firm*—Hill, Van Santen, Steadman & Simpson

[57] ABSTRACT

A shock wave head for non-contact disintegration of a calculi situated in the body of a life form comprises a shock wave generator for generating a shock wave essentially in one plane, and a lens arrangement received in a shock wave tube for focussing the shock wave into an in-focus range in a target region. The lens arrangement is mounted for adjustable movement in the shock wave tube from an extended position against a stop on the shock wave tube so that the arrangement can yield in the direction towards the shock wave generator when it is contacted by a patient being treated.

5 Claims, 1 Drawing Sheet

SHOCK WAVE HEAD FOR NON-CONTACTING DISINTEGRATION OF CALCULI

BACKGROUND OF THE INVENTION

The present invention is directed to a shock wave head for non-contacting disintegration of a calculus situated in the body of a life form. The shock wave head includes a shock wave generator for generating a shock wave in essentially one plane and a lens arrangement which is for focussing the shock wave onto a region of focus in a target region. Shock wave heads of this type are utilized in medicine, for example for destroying stones in the kidneys of a human. Since they avoid any and all entry into the body, they are especially advantageous and do not require the need of surgery.

A shock wave head, which comprises a shock wave tube composed of a jacket, of a shockwave generator having a flat coil and a copper membrane separated by an insulating foil, is disclosed in U.S. Pat. No. 4,674,505, whose disclosure is incorporated by reference and which claims priority from German Patent Application No. 33 28 051. In this device, an acoustical positive lens was adjustably arranged in the shock wave tube, and this lens focussed the planar shock wave generated by the membrane into a focal point. For the purpose of coupling the shock wave tube to the patient, the opening of the shock wave tube lying opposite the membrane is closed with a flexible sack or bag which, like the entire shock wave tube, is filled with a coupling agent. For coupling, the shock wave tube is moved in the direction towards the patient until the calculus to be destroyed is situated in the focal point of the lens arrangement. The bag or sack filled with the coupling fluid is placed against the surface of the patient so that it is guaranteed that the shock wave always proceeds within the coupling fluid until it enters the body.

With an obese patient, problems have occurred because the calculus to be destroyed lies so far inside the body of the patient that the focal distance of the lens arrangement is no longer adequate. As a result of this problem in a coupling procedure, the shock wave tube or, respectively, the lens arrangement contacts the patient and even pushes a portion of the patient aside or out of the way, given continuation of the coupling procedure. As a result thereof, the calculus is often moved out of an in-focus range or region so that a treatment can no longer be carried out.

SUMMARY OF THE INVENTION

The object of the present invention is to provide a shock wave head having a shock wave generator and lens arrangement that has a range of application for the shock wave head that is expanded so that obese patients can also be treated.

This object is achieved by an improvement in a shock wave head for non-contacting disintegration of calculi situated in the body of a life form comprising a shock wave generator generating shock waves in essentially one plane and having a lens arrangement for focussing the shock waves to an in-focus range in a target region. The improvements are that the lens arrangement is adjustably positioned against a first stop at one end of a shock wave tube by means for displaceably mounting and by means for yieldingly urging so that the lens arrangement can yield in the direction towards the shock wave generator when it comes in contact with the patient.

It, therefore, is achieved that it is not the patient who is moved during the coupling procedure so that the calculus migrates out of the in-focus range, but rather the lens arrangement yields so that the in-focus range is moved back towards the shock wave head. The calculus, however, continues to lie within the in-focus range so that it can be destroyed when shock waves are triggered.

It is proven advantageous when the lens arrangement is pressed against the stop by a spring. A migration of the calculus out of the in-focus range is prevented when the regulating distance for the lens arrangement is limited by a second stop and when it amounts to a few centimeters. This regulating distance essentially corresponds to the distance of the focus for the in-focus range.

Other features and advantages will be readily apparent from the following description of the preferred embodiments, the drawing and claims.

DESCRIPTION OF THE PREFERRED EMBODIMENTS

Figure 1:
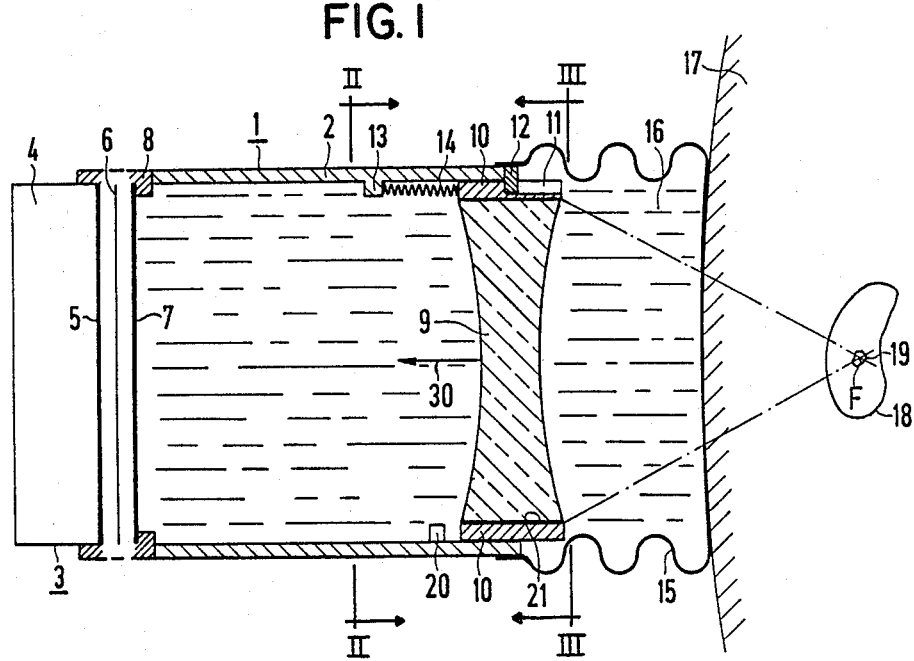
FIG. 1 is a cross sectional view of a shock wave head in accordance with the present invention.

The principles of the present invention are particularly useful when incorporated in a shock wave head, generally indicated at 1 in FIG. 1.

The head 1 comprises a liquid-filled, for example water-filled, jacket 2, whose one end is closed by a shock wave generator 3 that is composed of a coil carrier 4, a flat coil 5, an insulating foil 6 and a membrane 7, which are held pressed tightly against one another by a retaining ring 8. For purposes of illustration, the flat coil 5, the foil 6 and the membrane 7 are each shown with a spacing from one another.

Figure 2:
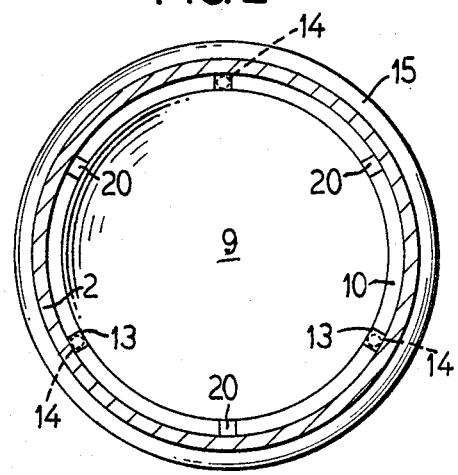
FIG. 2 is a cross sectional view taken on lines II—II of FIG. 1.
Figure 3:
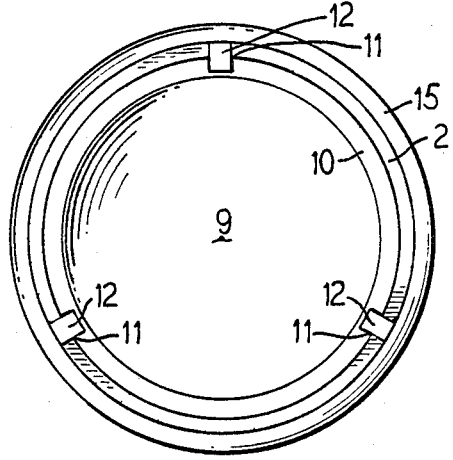
FIG. 3 is a cross sectional view taken on lines III—III of FIG. 1.

The other opening of the jacket 2 of the shock wave head 1 is covered by a lens arrangement 9 which has the function of an acoustical positive lens that is mounted in an annular mount 10. The mount 10 has a plurality of channels 11 (see FIG. 3) on a circumference which, beginning roughly at the center of the mount 10 (see FIG. 1), extend away from the shock wave generator 3. The jacket 2 has a plurality of noses forming first stops 12 (see FIG. 3), which are received in the channels 11. The mount 10 and the lens arrangement 9 are pressed against the first stops 12 by biasing means, which are illustrated as comprising a plurality of compression springs 14 (see FIGS. 1 and 2), which act against additional noses or projections 13.

The jacket 2, the shock wave generator 1 and the lens arrangement 9 are covered by a flexible bag or sack 15, which is filled with the coupling fluid 16. In a coupled condition, the bag 15 lies pressed against the skin of a patient 17. The calculus or stone 19, which is situated in the kidney 18, is then located in the focal point F of the lens arrangement 9 so that it can be destroyed by a shock wave generated by the shock wave generator 3.

When, however, the patient 17 is so obese that the distance from the skin to the kidney 18 and, thus, to the calculi or stone 19 is greater than the in-focus range, the surface of the patient 17 can be moved to come in contact with the lens arrangement 9. The lens arrangement 9 then will be displaced at a direction of arrow 30 toward the shock wave generator 3 against the force of the springs 14 during the coupling procedure. This displacement in the direction of arrow 30 can occur as long as the calculus 19 still lies within the in-focus range. Since the in-focus range exhibits a dimension of a few centimeters in the longitudinal direction of the shock wave head 1, the lens arrangement 9 can be displaced to the same degree without having the calculus 19 migrate out of the in-focus range. A second stop 20, against which the mount 10 of the lens arrangement 9 strikes, provides the limitation for the axial shifting of the lens arrangement. The second stop 20 is provided on an inner circumference of the jacket 2, as illustrated.

A fine positioning of the stop 20 allows the lens arrangement 9 to be displaced in a direction towards the focal point F relative to the mount 10 and, thus, relative to the jacket 2 of the shock wave head 1.

Each of the stops 12 and 20 can be provided with limit switches. For example, a limit switch at the first stop 12 will be actuated upon displacement of the lens arrangement 9 so that the person operating the device can be shown that the lens arrangement 9 is being moved out of its final, extended position and, thus, the calculus is no longer situated within the focus with the maximum, given complete coupling, but is now only situated within the in-focus range. When, by contrast, the lens arrangement 9 is moved against the second stop 20, then the coupling procedure can be immediately interrupted and the operating personnel will simultaneously be shown, for example on the monitor, that a coupling cannot occur, since the calculi 18 will lie outside of the in-focus range.

Although various minor modifications may be suggested by those versed in the art, it should be understood that I wish to embody within the scope of the patent granted hereon all such modifications as reasonably and properly come within the scope of my contribution to the art.

I claim:

1. In a shock wave head for non-contact disintegration of calculi situated in the body of a life form, said shock wave head comprising a shock wave tube having a shock wave generator for generating shock waves in essentially one plane, and a lens arrangement for focussing the shock waves to an in-focus range in a target region, the improvements comprising said shock wave tube having a first stop at one end of the tube, means for displaceably mounting said lens arrangement at said one end of said shock wave tube, and means for yieldably urging the lens arrangement against said first stop so that when the lens arrangement is contacted by a patient it can move in said tube in a direction toward the shock wave generator and away from said first stop.

2. In a shock wave head according to claim 1, wherein said shock wave tube has a second stop spaced inward from the one end and the first stop so that the distance of the movement of the lens arrangement from the first stop towards the shock wave generator is limited by the second stop with the amount of movement being a few centimeters.

3. In a shock wave head according to claim 1, wherein the means yieldingly urging include at least one spring acting between the shock wave tube and the lens arrangement.

4. In a shock wave head according to claim 3, wherein a second stop is provided in the shock wave tube in spaced relationship to the first stop to limit the distance of movement of the lens arrangement towards the shock wave generator to a few centimeters.

5. In a shock wave head for non-contact disintegration of calculi situated in the body of a life form, said shock wave head comprising a shock wave tube having a shock wave generator for generating shock waves in essentially one plane, and a lens arrangement for focussing the shock waves to an in-focus range in a target region, the improvement comprising the shock wave tube having a first stop at one end and a second stop spaced inward of the first stop, means for mounting the lens arrangement in the tube for movement between said first and second stops and spring means for biasing the lens arrangement against the first stop so that when the one end of the tube is moved against a patient, the lens arrangement can be shifted toward the second stop.

* * * * *